US007390515B2

(12) United States Patent
Weiss et al.

(10) Patent No.: US 7,390,515 B2
(45) Date of Patent: Jun. 24, 2008

(54) METHODS OF TREATING VIRAL INFECTIONS USING BERRY JUICE FRACTIONS

(75) Inventors: Ervin I. Weiss, Herzeliya (IL); Itzhak Ofek, Givataim (IL); Zichria Zakay-Rones, Jerusalem (IL); Yael Houri-Haddad, Modiin (IL)

(73) Assignee: Ramot At Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 11/069,041

(22) Filed: Mar. 2, 2005

(65) Prior Publication Data

US 2005/0196472 A1 Sep. 8, 2005

(51) Int. Cl.
*A61K 36/04* (2006.01)
(52) U.S. Cl. ..................................... 424/732
(58) Field of Classification Search ............... 424/732
See application file for complete search history.

(56) References Cited

U.S. PATENT DOCUMENTS

| 5,474,774 | A | 12/1995 | Walker et al. |
| 5,840,322 | A | 11/1998 | Weiss et al. |
| 6,303,125 | B1 | 10/2001 | Ofek et al. |
| 6,843,993 | B2 | 1/2005 | Ofek et al. |
| 2003/0149252 | A1* | 8/2003 | Gourdin et al. ............ 536/8 |
| 2003/0236300 | A1* | 12/2003 | Caplan et al. ............ 514/456 |

OTHER PUBLICATIONS

Prior, R. L.; Lazarus, S. A.; Cao, G.; Muccitelli, H.; Hammerstone, J. F. J. Agric. Food Chem. 2001; 49: 1270-1276.*
Carson, R. S.; Frisch, A. J. Bacteriol. 1953; 66(5): 572-575.*
http://www.sciencedirect.com/science?_ob=IssueURL&_tockey=%23TOC%234919%232003%23999429996%234175
47%23FLA%23&_auth=y&view=c&_acct=C000055109
&_version=1
&_urlVersion=0&_userid=2502287
&md5=217cc2c3c74dc634fa4cbfccea84952f (Accessed Mar. 23, 2006).*
http://www.ncbi.nlm.nih.gov/entrez/query.fcgi?cmd=Retrieve
&db=pubmed&dopt=Abstract&list_uids=8206868&query_hl=5
&itool=pubmed_DocSum (Accessed Mar. 23, 2006).*
Abstract. Fokina G.I.; Roikel, M.P.; Frolova, M.P.; Frolova, T.V.; Pogodina, V.V. Vopr Virusol. 1993; 38(4): 170-173.*
Kaufman, S.R. Perspectives on Medical Research. vol. 4, 1993, p. 12.*
Prior, R.L.; Lazarus, S.A.; Cao, G.; Muccitelli, H.; Hammerstone, J.F. J Agric Food Chem. 2001; 49: 1270-1276.*
Carson, R.S.; Frisch, A.J. Bacteriol. 1553; 66(5): 572-575.*
http://www.sciencedirect.com/science?_ob=IssueURL&_tockey=%23TOC%234919%232003%23999429996%234175
47%23FLA%23&_auth=y&view=c&_acct=C000055109
&_version=1&_urlVersion=0&_userid=2502287
&md5=217cc2c3c74dc634fa4cbfccea84952f.* http://www.ncbi.nlm.nih.gov/entrez/query.fcgi?cmd=Retrieve
&db=pubmed&dopt=Abstract&list_uids=8206868&query_hl=5
&itool=pubmed_DocSum.*
Gu L., Kelm M., Hammerstone, J. F., Beecher G., Cunningham D., Vannozzi S., Prior R. L. J. Agric. Food Chem. 2002; 50: 4852-4860.*
Bagchi D., Sen C.K, Bagchi M., Atalay M. Biochem (Moscow). 2004; 69 (1): 75-80.*
Abstract. Fokina G.I.; Roikel, M.P.; Frolova, M.P.; Frolova, T.V.; Pogodina, V.V. Vopr Virusol. 1993; 38(4): 170-173.*
Cox et al. "Influenza virus: immunity and vaccination strategies. Comparison of the immune response to inactivated and live, attenuated influenza vaccines". Scand J Immunol. Jan. 2004;59(1):1-15.*
Kawaoka. "Equine H7N7 Influenza A Viruses are Highly Pathogenic in Mice without Adaptation: Potential Use as an Animal Model", J. of Virol. vol. 65, No. 7 (Jul. 1991) 3891-3894.*
http://en.wikipedia.org/wiki/Paramyxoviridae.*
http://en.wikipedia.org/wiki/influenza_virus.*
(U1) "Viruses and Bacteria" Apr. 8, 2000 (Internet Archieve Date) (Retrieved on Oct. 12, 2008). Retrived from the Internet:<http://web.archive.org/web/*/http://www.netdoctor.co.uk/health_advice/facts/virusbacteria.htm>.*
(V1) Abstract. Fokina G.I.; Roikel, M.P.; Frolova, M.P.; Frolova, T.V.; Pogodina, V.V. Vopr Virusol. 1993; 38(4): 170-173.*
(W1) Kaufman, S.R. Perspectives on Medical Research. vol. 4, 1993, p. 12.*
Ofek, I. et al., "Anti-*Escherichia coli* Adhesin Activity of Cranberry and Blueberry Juices", *New Eng. J. Med.*, vol. 324, No. 22, pp. 1599 (1991).
Ahuja, S. et al., "Loss of Fimbrial Adhesion With the Addition of *Vaccinum Macrocarpon* To The Growth Medium of P-Fimbriated *Escherchia coli*", *J. Urol.*, vol. 159, pp. 559-562 (Feb. 1998).
Burger, O et al., "A high molecular mass constituent of cranberry juice inhibits *Helicobacter pylori* adhesion to human gastric mucus", *FEMS Immunol. Med. Microbiol.*, vol. 29. pp. 295-301 (2000).
Foo, L.Y., "The structure of cranberry proanthocyanidins which inhibit adherence of uropathogenic P-fimbriated *Escherichia coli* in vitro", *Phytochemistry*, vol. 54, pp. 173-181 (2000).
Weiss, E.I. et al. "Inhibiting Interspecies Coaggregation of Plaque Bacteria With a Cranberry Juice Constituent", *JADA*, vol. 129, pp. 1719-1723 (1998).

(Continued)

*Primary Examiner*—Christopher R. Tate
*Assistant Examiner*—Amy L. Clark
(74) *Attorney, Agent, or Firm*—The NATH LAW Group; Susanne M. Hopkins; Ari G. Zytcer

(57) ABSTRACT

The present invention concerns the use as anti-viral agents of isolated fractions from berry juice of the plant genus *Vaccinium*. Two specific fractions are provided: (a) polymeric material having a molecular weight≧12,000; and (b) proanthocyanidins-containing fraction.

Thus, the invention provides methods of treating a subject against a viral infection; the method comprises providing said subject with at least one of the above isolated fractions in an amount effective to prevent production of a viral infection in said subject.

A specific and preferred viral infection according to the invention is an influenza virus infection.

10 Claims, 2 Drawing Sheets

OTHER PUBLICATIONS

Zafriri, D. et al., "Inhibitory Activity of Cranberry Juice on Adherence of Type 1 and Type P Fimbriated *Escherichia coli* to Eucaryotic Cells", *AntiMicrob. Agents Chemothe.*, vol. 33, No. 1, pp. 92-98 (Jan. 1989).

Weiss, E.I. et al., "A high molecular mass cranberry constituent reduces mutans streptococci level in saliva and inhibits in vitro adhesion to hydroxyapatite", *FEMS Microbiol Lett.*, vol. 232, pp. 89-92 (2004).

Foo, L.Y. et al., "A -Type Proanthocyanidin Trimers from Cranberry that Inhibit Adherence of Uropathogenic P-Fimbriated *Escherichia coli*" J. Nat. Prod., vol. 63, pp. 1225-1228 (2000).

* cited by examiner

METHODS OF TREATING VIRAL INFECTIONS USING BERRY JUICE FRACTIONS

FIELD OF THE INVENTION

This invention relates to fractions isolated from Vaccinium plants berries having an anti-viral activity. Specifically, to isolated fractions from cranberry juice which have anti-viral characteristics.

PRIOR ART

The following is a list of prior art which is considered to be pertinent for the state of the art in the field of the invention.
Ofek, I., et al. *New Eng. J. Med.* 324:1599 (1991);
Ahuja, S., et al., *J. Urol.* 159:559-562 1998;
Burger, O., et al. *FEMS Immunol. Med. Microbiol.* 29:295-301 (2000);
Foo, L. Y., et al. *Phytochemistry* 54:173-181 (2000(a));
Weiss, E. I., et al. *JADA* 129:1719-1723 (1998);
Zafriri, D., et al. *AntiMicrob. Agents Chemothe.* 33:92-98 (1998);
Weiss E. I., et al. *FEMS Microbiol Lett.* 232:89-92 (2004);
Foo, L. Y. et al. *Escherichia coli J. Nat. Prod.*, 63:1225-1228 (2000(b))
U.S. Pat. No. 5,840,322;
U.S. Pat. No. 6,303,125;
U.S. Pat. No. 6,843,993;
U.S. Pat. No. 5,474,774.

BACKGROUND OF THE INVENTION

Myxoviridae

Influenza viruses belong to a broad family of RNA viruses, the Orthomyxoviridae (myxo=mucus) viruses. Orthomyxoviridae viruses as well as the closely related family or RNA viruses, Paramyxoviridae viruses, are characterized by a negative-stranded RNA genome (segmented or non-segmented, respectively), having, an inner ribonucleoprotein (RNP) core surrounded by a lipid bilayer membrane from which spikes protrude. The spikes are of three kinds: a hemagglutinin (HA) which agglutinates erythrocytes, an enzyme neuraminidase (NA) which releases the virus from cells and a small number of copies of the M2 protein that serves as an ion channel. These spikes in influenza (in Parmyxoviridae virus these are HN and F) are involved in hemagglutination, hemolysis of erythrocytes etc. and cleavage of the receptor (on the cell) anti-receptor (on the virus) bond, and reflect the ability of the virus to enter the nucleoprotein core into cells.

Influenza is a highly communicable acute respiratory disease that predisposes to a number of complications, resulting in a severe world-wide economic burden. Prevention and control of both the annual influenza epidemics and its infrequent but severe pandemic outbreaks are hitherto achieved by the use of vaccines and newly emerging antiviral drugs.

Unfortunately, the vaccines provide sometimes lower than desirable protection, particularly in the immuno-compromised and the elderly, the two most susceptible subpopulations (Keren. G., et al. *J. Med. Virol.* 25:85-89 (1988); Admon, D., et al. *Vaccine* 15:1518-1522 (1997)). Furthermore, the vaccines currently available are designated for intramuscular injection, resulting mainly in serum antibodies.

As to antiviral drugs, two classes of antiviral drugs are used:

(i) Anti-M2 inhibitors amantadine and rimantadine, effective against A strains only (World Health Organization, WHO Org. Rep. Ser., Geneva. 642:1-63 (1980)). A reduction in the severity and duration of the signs and symptoms is recorded when they are administered within 48 hrs of disease onset (Centers for Disease Control and Prevention, 1996. Prevention and control of influenza: Recommendation of the advisory committee on immunization practices (ACIP). MMWR45(RR-5), 1-24);

(ii) Neuraminadase inhibitors, effective against both A and B viruses. As prophylactics, these inhibitors are 70-90% effective and may shorten the duration of illness by 1.5 days when used within the first 48 hr (Treanor, J., Falsey, A., *Antiviral Res.* 44:79-102 (1999)).

Vaccinium Genus

Vaccinium is a genus of evergreen or deciduous berry-bearing ericaceous shrubs including the various kinds of blueberries and the true cranberries.

Physicians have long recommended consumption of cranberry juice to avoid urinary tract infections. It was hypothesized that the prevention of bacterial infections is due to the inhibition of *E. coli* adhesion to uroepithelial cells by cranberry constituents (Ofek et al., 1991, ibid.). Studies have shown that cranberries contain high and low molecular weight constituents [nondialyzable material (NDM) and proanthocyanidins, respectively], which act in vitro to inhibit the adhesion of diverse microbial species (Ahuja et al., 1998 ibid.; Burger et al., 2000, ibid.; Foo et al., 2000a, ibid.; Weiss et al., 1998 ibid.; Zafriri et al., 1998, ibid). It has been suggested that cranberry proanthocyanidins are one of the active anti-adhesion agents (Foo et al., 2000a, ibid.).

SUMMARY OF THE INVENTION

The present invention is based on the finding that fractions, isolated from cranberry juice, exhibit anti-viral activity. This anti-viral activity was demonstrated in vitro, by preventing virus adsorption to red blood cells thus inhibiting hemagglutination (HA) and to cells in cultures interfering in virus propagation in host cells, as well as in vivo, by exhibiting an increased survival rate of infected mice. Thus, it was envisioned that fractions from juice from berries of the plant genus *Vaccinium* may be have a beneficial effect against viral infections.

Thus, according to a first aspect, the invention provides a method of treating a subject against a viral infection, the method comprises providing said subject with an amount of a polymeric material having a molecular weight $\geq$12,000-14,000 and isolated from juice from berries of the plant genus *Vaccinium*, the amount of said polymeric material being effective to prevent production of a viral infection in said subject.

According to second aspect, the invention provides a method of treating a subject against a viral infection comprising providing said subject with an amount of a proanthocyanidins-containing fraction isolated from juice from berries of the plant genus *Vaccinium*, the amount of said proanthocyanidins-containing fraction being effective to prevent production of viral infection in said subject.

A specific and preferred viral infection according to the invention is an influenza virus infection.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

Figure 1:
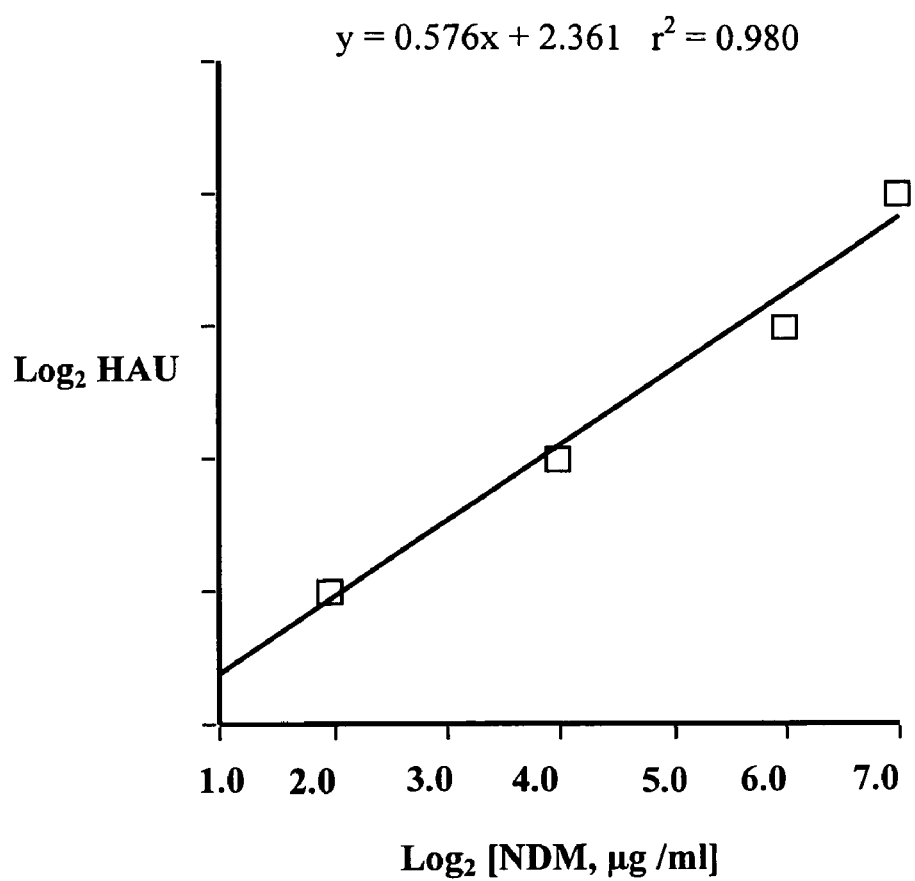
FIG. 1 is a graph showing the dose dependent effect of NDM on inhibition of virus HA activity.

FIG. 2 is an image showing the prevention of virus-induced cytopathic effect by NDM, and in which MDCK monolayers were inoculated with B/Yamanashi virus suspension (rows A, B and C) only or with a mixture of NDM (250 μg/ml) and B/Yamanashi/166/98 virus, (rows D, E and F). Blue staining (observed as darker wells) indicates that the cells are intact; staining is not obtained if the cells are destroyed.

FIG. 3 is a bar graph showing the levels of INFγ in the serum of mice following influenza challenge and NDM treatment.

DETAILED DESCRIPTION OF THE INVENTION

According to a first aspect, the invention provides a method of treating a subject against a viral infection; the method comprises providing the subject with an amount of a polymeric material having a molecular weight≧12,000-14,000 kDa, preferably≧14,000 kDa and isolated from juice from berries of the plant genus *Vaccinium*, the amount of said polymeric material being effective to prevent production of a viral infection in said subject. Due to the relatively high molecular weight of the substances forming part of this isolated polymeric material, this aspect of the invention is referred to herein by the term "non-dialyzable material aspect", or "NDM aspect" of the invention.

According to a second aspect, the invention provides a method of treating a subject against a viral infection; the method comprises providing said subject with an amount of a proanthocyanidins-containing fraction isolated from juice from berries of the plant genus *Vaccinium*, the amount of said proanthocyanidins-containing fraction being effective to prevent production of viral infection in said subject. Due to the proanthocyanidins content in this isolated fraction, this aspect of the invention is referred to herein by the term "proanthocyanidins aspect" or "PAC aspect" of the invention.

Notwithstanding the above, when appropriate, the isolated polymeric material, according to the NDM aspect of the invention, and the proanthocyanidins-containing fraction, according to the PAC aspect of the invention, are collectively referred to by the term "isolated fraction".

The isolated fraction according to the invention comprises at least one of the following characteristics:

- it is capable of inhibiting viral induced hemagglutination;
- it is capable of inhibiting viral adsorption to a susceptible host cell;
- it is capable of inhibiting viral penetration into a susceptible host cell (e.g. by endocytosis);
- it is capable of inhibiting viral replication, thereby preventing propagation of viral progenies.

The isolated fraction is effective for treatment of a subject against a viral infection. According to the present invention the term "treatment" denotes any physiological effect resulting in the therapeutic treatment of a viral infection or prevention (prophylactic treatment) of the formation of a viral infection in a subject exposed to an infectious virus. Thus, in the context of the present invention, treatment refers to at least one of the following: inhibition of viral adsorption to susceptible cells, inhibition of viral penetration into susceptible cells, inhibition of viral replication, all of which result in a decrease in viral load (thereby less antibody response) in an infected subject, preferably, total elimination of the virus from the subject. Treatment preferably results in the improved and more rapid recovery of the subject from the viral infection or the prevention of the infection from occurring.

The effective amount of each of the isolated fraction, i.e. the polymeric material as well as the proanthocyanidins-containing fraction, is determined by such considerations as may be known in the art. The amount must be effective to achieve the desired therapeutic or prophylactic effect described above. The amount is typically determined in appropriately designed studies and the person versed in the art will know how to properly conduct such studies in order to determine the required effective amount.

With respect to the NDM aspect of the invention a typical concentration range of the polymeric material in a single dose administered to a subject in need is between 1 μg/ml and 5 mg/ml within a suitable physiologically acceptable carrier, with a preferred concentration between 10 μg/ml and 500 μg/ml. With respect to the PAC aspect of the invention a typical concentration range of the proanthocyanidins-containing fraction in a single dose administered to a subject in need is between 5 μg/ml and 500 μg/ml within a suitable physiologically acceptable carrier.

The isolated fraction according to the invention may be obtained from any member of the plant genus *Vaccinium*. As well appreciated by those versed in the art of botanic, the *Vaccinium* consists of about 450 species of evergreen and deciduous shrubs. Some kinds are grown for the beauty of their fall leaves and some for their attractive flowers and deliciously edible fruits. Many different names have been given to the numerous varieties that produce edible fruits which may be used in accordance with the present invention. Some non-limiting examples include the Blueberry, Bilberry, Cowberry, Cranberry, Crowberry; Farkleberry, Lingonberry, Partridgeberry, Huckleberry Whortleberry, and Sparkleberry.

The invention makes use of isolated fraction which may be obtained from berries juice as well as from berries juice concentrates. Berries juice and berries juice concentrates may be prepared by methods known in the art or obtained from commercially available products. A specific and preferred juice is cranberry juice which is commercially available.

According to the NDM aspect of the invention, the isolated polymeric material may be obtained and is characterized as described by Ofek, I., et al. (Ofek et al. et al. Adv. Exp. Med. Biol. 408:179-183 (1996); and U.S. Pat. Nos. 6,303,125, 5,840,322 and 6,843,993, all of which are incorporated herein by reference in their entirety). Accordingly, the isolated polymeric material is further characterized by at least one of the following parameters:

- it has an elemental analysis of carbon 43-51%, hydrogen 4-5%, no nitrogen, no sulfur and no chlorine, preferably 56.6% carbon and 4.14% hydrogen;
- it has a characterizing NMR fingerprint spectrum as set forth in the aforementioned U.S. Pat. Nos. 6,303,125, 5,840,322 and 6,843,993, all being incorporated herein by reference in their entirety;
- it has an ultraviolet spectrum with an absorption peak at 280 nm in neutral or acidic pH solution which is absent in alkali solutions.
- it exhibits tannin-like properties;
- it is highly soluble in water;
- it is devoid of proteins, carbohydrates and fatty acids;
- it has less than 0.02 mg/ml of phenolic residues at a concentration of 0.1 mg/ml.

As should be appreciated, there are many alternative ways to produce a polymeric material, having one or more of the aforementioned physical and chemical characteristics. According to one embodiment of the invention, the polymeric material is obtained by subjecting cranberry juice or cranberry juice concentrate (as an exemplar species of *Vaccinium*) to dialysis at against double distilled water (ddWater) using dialysis tubing with a≧12,000 kDa-14,000 kDa molecular cut-off and collecting the non-dialyzable material (NDM) remaining in the dialysis tubing. This remaining NDM may then be lyophilized to obtain a dry powder which may be fractionated on a resin, e.g. polyacrylamide resin column. The active polymeric material may then be eluted from the column with water and once again lyophilized to obtain a dry polymeric material.

The non-dialyzable material, NDM, was assayed for polyphenol compounds as follows:

Polyphenol Assay: A modified Folin-Denis test [Folin and Denis, 1912] was used to detect all hydroxylated phenolic compounds [Mehansho et al, 1987]. As a control standard commercially available tannin and anthocyanin was obtained from Sigma Chemical Co. (St. Louis, Mo.). The test was sensitive for phenolic compounds concentrations down to 0.02 mg/ml tanin in standard Results: NDM at 0.1 mg/ml concentration (repeated twice) showed less than 0.02 mg/ml of phenolic residues. Therefore, NDM does not contain phenolyic residues found typically in tannins and anthocyanins by this test.

Referring to the PAC aspect of the invention, the proanthocyanidins-containing fraction is further characterized by one or more of the following characteristics:

it is enriched with polyphenol and flavonoid compounds;
it has a characteristic elution peaks at 230 nm, 280 nm, and 360 nm, as described by Foo et al. [Foo L. Y., et al. 2000(a); Foo L. Y., et al. 2000(b)], incorporated herein by reference in its entirety;
it has a benzoic acid content of less than about 0.01 per gram dry powder as described by Foo et al. [Foo L. Y., et al. 2000(a); Foo L. Y., et al. 2000(b)], incorporated herein by reference in its entirety.

The proanthocyanidins-containing fraction may be obtained as described by Foo et al. [Foo L. Y., et al. 2000(a); Foo L. Y., et al. 2000(b)], incorporated herein by reference in its entirety. Further, the proanthocyanidins-containing fraction is commercially available, and may be obtained, for example, from Ocean Spray [Ocean Spray Cranberries, Inc, Lakeville-Middleboro, Mass. 02349].

The viral infection according to the invention is an infection preferably localized within the respiratory tract, either the upper respiratory tract, lower respiratory tract, or both. Non-limiting examples of viruses causing an infectious disease within the respiratory tract include members of the Orthomyxoviridae family or Paramyxoviridae family of viruses.

According to one embodiment, the virus causing the infection is a member of the Orthomyxoviridae family. According to a specific embodiment, the virus is selected from Influenza viruses.

According to another embodiment, the virus is a member of the Paramyxoviridae family. According to one embodiment, the virus is selected from Para-Influenza Types 1, 2, 3 and 4 Virus and Respiratory Syncytial Virus (RSV). Other members of the group include Human metapneumovirus and Newcastle Disease Virus (NDV) which infect poultry.

According to yet another embodiment of the invention, the virus is characterized by infecting cells carrying on their surface receptors comprising sialyl sugar chains, the sialyl sugar chains bearing receptors being involved in the adsorption of the virus onto the susceptible cell thereby causing infection. Sialyl sugar-chains bearing receptors are found, inter alia, on the surface of influenza virus as well as on the surface of other viruses, all forming part of the present invention.

It is commonly known that viral infections may be transmitted from animals to humans. Thus, the invention is also applicable for treating subjects where the virus is an animal-type virus being transmitted from an animal to humans. For example, it is known that influenza A virus may be found in many animals, such as ducks, chickens, pigs, whales, horses, and seals which may be transmitted to humans resulting in an infectious disease.

Further, the invention is applicable for treating non-human animals for a viral infection. A non-human animal viral infection of particular interest includes the Avian Influenza viruses (also known by the term "Bird Flu"). Avian influenza virus can be transfer to human with high morbidity rate and therefore a therapeutic treatment thereagainst is of high importance.

The isolated fraction may be administered in various ways suitable for anti-viral therapy. It should be noted that it can be administered as the extracted fraction per se (e.g. as a powder), or within a suitable carrier suitable for a selected delivery route. While the isolated fraction may be administered by any suitable route, e.g. orally, a preferred mode of administration of the isolated fraction according to the invention is by intranasal application, preferably, by inhalation.

According to one embodiment, the isolated fraction is administered in the form of a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's Pharmaceutical Sciences, Ed. By Arthur Osol, p. 1445 (1980)). Of course, the ordinary artisan can readily determine a suitable saline content and pH for an innocuous aqueous carrier for nasal administration.

Other, non-limiting examples of intranasal dosage forms containing the isolated fraction include nasal gels, creams, pastes or ointments with a viscosity of, e.g., from about 10 to about 3000 cps, or from about 2500 to 6500 cps, or greater, which may provide a more sustained contact with the nasal mucosal surfaces. Such carrier viscous formulations may be based upon, simply by way of example, polymeric carriers such as alkylcelluloses and/or other biocompatible carriers of high viscosity well known to the art (see e.g., Remington's, cited supra). The carrier containing the isolated fraction may also be soaked into a fabric material, such as gauze, that can be applied to the nasal mucosal surfaces to allow for active substances in the isolated fraction to penetrate to the mucosa.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation.

Further, for nasal administration of solutions or suspensions of the isolated fraction, various devices are available in the art for the generation of drops, droplets and sprays. For example, solutions comprising the isolated fraction can be administered into the nasal passages by means of a simple dropper (or pipet) that includes a glass, plastic or metal dispensing tube from which the contents are expelled drop by drop by means of air pressure provided by a manually powered pump, e.g., a flexible rubber bulb, attached to one end. Fine droplets and sprays can be provided by a manual or electrically powered intranasal pump dispenser or squeeze bottle as well known to the art, e.g., that is designed to blow a mixture of air and fine droplets into the nasal passages.

The following examples, which are in no way intended to limit the scope of the present invention, illustrate the preparation of cranberry isolated fractions and their effect against influenza virus infection. Obviously, many modifications and variations of the present invention are possible in light of the above teaching. It is therefore, to be understood that within the scope of the appended claims, the invention may be practiced otherwise than as specifically described hereinbelow.

SPECIFIC EXAMPLES

In the following examples, the activity of NDM on influenza virus-mediated red blood cells (RBC) hemagglutination (HA), in vitro replication of the virus and in vivo infectivity of the virus, were tested.

Cranberry Juice

Cranberry juice from the American cranberry, *Vaccinium macrocarpon*, and a proanthocyanidin-rich fraction were obtained from Ocean Spray, Inc. [Ocean Spray Cranberries, Inc, Lakeville-Middleboro, Mass. 02349]

To obtain the polymeric material having molecular weight≧12,000 kDa, the juice was dialyzed at 4° C. for 10 days against distilled water, changed ten times, in dialysis bags of≧12,000-14,000 MW cut-off and lyophilized. The non-dialyzable material (NDM) exhibits tannin-like properties, is highly soluble in water, devoid of proteins, carbohydrates and fatty acids and contains 56.6% carbon and 4.14% hydrogen (Ofek et al., 1996, ibid).

Influenza Virus

The following influenza virus strains were used:
1. A/PR/8/34 $H_1N_1$ grown in the allantoic sac of 10-11-day-old cells eggs to a 1:1024-2048 HA titer, or grown in Madine-Darby canine kidney (MDCK) cells to a 1:128 HA titer.
2. A/$H_1N_1$ (1:128 HA titer) and A/$H_3N_2$ (1:256 HA titer), clinical isolates grown in MDCK cells.
3. A/Panama 2007/99 $H_3N_2$ adapted to MDCK cells (1:256HA titer)
4. B/Yamanashi/166/98, grown in MDCK cells (1:256-512 HA titer). To evaluate replication inhibition, viruses cultivated in MDCK cells were used.

To determine HA, 0.1 ml of twofold dilutions of each virus suspension in phosphate-buffered-saline (PBS) was mixed with 0.1 ml of a 0.5% chicken RBC or 1% sheep RBC or human 1% O RBC suspension and scored after 30 min incubation at room temperature (Sever, J. L., *J. Immunol.* 88:320-329 (1962)).

HA Determination

The HA data are summarized in the following Table 1:

TABLE 1

Viral Hemmagglutination and replication in NDCK cells

| Viral stain | | HAU [a] | | MDCK cells (log 10) [b] | |
|---|---|---|---|---|---|
| | | Untreated | Treated | Untreated | Treated |
| A/PR8/34 | (i) egg | 16 | <1 | NP | NP |
| | (ii) MDCK | 16 | 2-4 | 6.5 | 1.5 |
| A/$H_3N_2$ | | 16 | 4-8 | 6.5 | 1.5 |
| A/H1N1 | | 16 | 4-8 | 6.0 | 1.5 |
| B/Yamanashi/166/98 | | 16 | <1 | 7.5 | 1.5 |
| A/H5N3 (Avian) | | 16 | 2-4 | 6.5 | 2.5 |

[a] Hemagglutination units of treated virus (preincubated with 125 µg/ml of NDM), compared with that of untreated virus.
[b] $TCID_{50}$ (Tissue Culture Infecting Dose) in MDCK cells of treated virus (preincubated with 250 µg/ml of NDM), compared with that of untreated virus.
NP = not performed Preincubation of NDM (125 µg/ml) with A/PR/8 (egg-grown) or B/Yamanashi (grown in MDCK cells) strains inhibited virus-induced HA. This was reduced from 16 HA units (HAU) to <1 in NDM-containing virus suspensions (100%). NDM at 125 µg/ml reduced the 16 HAU of the two clinical isolates A/$H_1N_1$ and A/$H_3N_2$ to 4-8 units. A/PR/8 grown in MDCK cells was less sensitive to 125 µg/ml NDM; the 16HAU were reduced to 2-4 HAU (Table 1).

A higher NDM concentration (400 µg/ml) was needed to reduce the HAU of the MDCK cell-grown A/PR/8 strain from 16 to <1 units (not shown). Chess board titration of virus densities and decreasing NDM concentrations revealed that as little as 4, 16, 64 and 128 µg/ml NDM were needed to completely inhibit HA induced by 8, 16, 32, 64 respectively, HAU of virus A/PR8/34. The results indicate a highly significant $r^2=0.980$ correlation between HAU and NDM concentration required to completely inhibit HA (FIG. 1). HA inhibition was also observed using sheep or human RBC, consistent with the notion that the target for NDM is the virus.

Virus Replication

Figure 2:
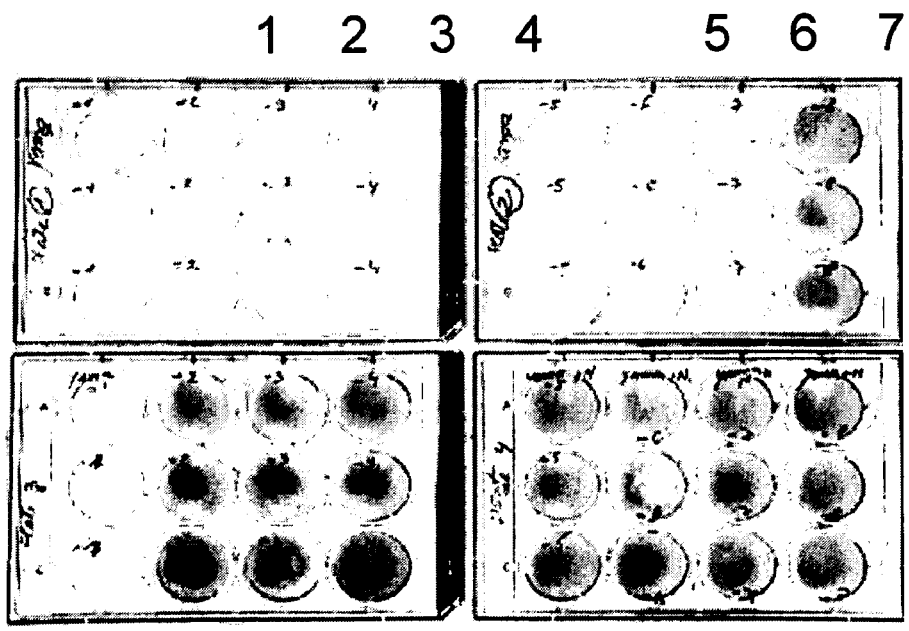

To test inhibition of virus replication, MDCK cells were grown in DMEM medium supplemented with 10% inactivated FCS and antibiotics (100µg/ml penicillin G and 100 µg/ml streptomycin). For the assay, cells were grown in 12-well culture plates (Nunc, Roskilde, Denmark) in a humidified atmosphere with 5% $CO_2$ at 37° C., and used when confluent monolayers had formed (48 hrs). NDM inhibition of virus infectivity in vitro was tested by incubating 250 µg/ml NDM with virus for 2 h at room temperature. Tenfold serial dilutions in medium without serum were inoculated in triplicate wells containing MDCK monolayers. The virus was allowed to adsorb for 1 hr at 37° C. The inoculum was removed and medium supplemented with 1% serum and trypsin 2 µg/ml (×2 crystallized) was added. Following 4 days incubation at 37° C. in a 5% $CO_2$ incubator, the monolayers were examined for cytopathic effect (CPE) (FIG. 2) and the respective supernatants were assayed for HA. HA was evident at a dilution of up to $10^{-7}$ in the control wells, whereas in wells infected with the virus-NDM suspension, hemagglutination was observed only at $10^{-1}$. For the CPE, the monolayers were washed with PBS to remove dead cells and debris, fixed with cold methanol and stained with crystal violet to determine the integrity of the monolayer. The CPE was observed in all the control wells (FIG. 2 rows A, B and C) at a $10^{-7}$ viral dilution whereas in the virus-NDM suspension the CPE was observed at $10^{-1}$ (FIG. 2 rows D, E and F). The observed CPE correlated with the HA results (not shown), allowing calculation of tissue culture infective dose ($TCID_{50}$, Reed, L. J., Muench, H. A., *Am. J. Hyg.* 27:493-497 (1938)).

NDM reduced the B/Yamanashi titer from $10^{7.5}$ to $10^{1.5}$ (Table 1). Significant inhibition of infectivity by NDM was demonstrated for all the virus strains tested (p<0.001, Fisher's Exact Test): the A/H$_3$N$_2$ was reduced from $10^{6.5}$ to $10^{1.5}$, A/H$_1$N$_1$ from $10^{6.0}$ to $10^{1.5}$ and A/PR8 (grown in MDCK cells) from $10^{6.5}$ to $10^{1.5}$ (Table 1). When A/H$_3$N$_2$ and NDM were added simultaneously, the TCID$_{50}$ titer dropped from $10^{6.5}$ to $10^{2.0}$ and from $10^{6.0}$ to $10^{1.5}$ when A/PR8 was tested. These data suggest that the NDM-virus interaction was virtually instantaneous and that pre-incubation is not required. Inhibition of infectivity in MDCK cells was similar for the A strains (4.5-5 logs), B/Yamanashi appeared to be more sensitive (6 logs).

Viral Infectivity

To evaluate the potential of the NDM in the therapy of viral infection, the cells were first exposed to viral suspensions to allow adsorption followed by penetration into the cells for 1 hr. NDM (100 μg/ml) was added at various post infection time intervals as indicated in Table 2. Viral TCID$_{50}$ was determined in the treated cultures following 4 days and 6 days incubation by assaying the supernatants for HA activity.

The results in Table 2 show that NDM reduced virus TCID$_{50}$ for the entire time of the follow up (6 days post infection). This effect was most accentuated when the NDM was added several times to the infected MDCK monolayer (Table 2). These results demonstrate that NDM can reduce or inhibit virus replication indicating inactivation of newly formed virus.

TABLE 2

Effect of NDM post infection

| Viral stain | Control | Time (h) of NDM treatment post viral adsorption[a] | | | |
|---|---|---|---|---|---|
| | | 1 | 6 | 24 | 1 + 6 + 24 |
| A/Panama H$_3$N$_2$ | 3.5/3.5 | <1/3 | 1.5/2.5 | 2/2.5[b] | <1/<1[c] |
| B/ Yamanashi | 4.5/4.5 | 2.5/3 | 2/3[b] | 3/3[b] | <1/1.5[c] |

[a]NDM, 100 μg/ml, was added in each treatment.
[b]Logistic regression at a confidence interval of 95% yielded odds of 42-91.
[c]Logistic regression at a confidence interval of 95% yielded odds of ≧2110.

The effect of cranberry proanthocyanidins-containing fraction was compared with that of NDM. A four- to fivefold higher proanthocyanidin concentration was required to completely inhibit 16HA units of A/PR8 (grown in egg), providing evidence that that NDM is significantly more potent (at least six times more active (weight per volume)) than cranberry proanthocyanidins.

Differentiation Between Cranberry Fractions

Comparing virus induced hemagglutination the anti-adsorption activity of three cranberry fractions:
 1. prothoantocyanidine (PAC)
 2. non dialyzable material (NDM) prepared cranberry from juice
 3. cranberry powder (CHEP) prepared from press-cake (CHEP is an Ocean Spray Inc. product now used by the NIH grantees of the NICCAM projects).

Hemagglutination caused by influenza virus reflects the activity of the viral adsorption which mediates attachment as the first event before entry of the virus into the cells. Thus agent(s) which inhibit hemagglutination caused by the virus are of potential therapeutic value.

Based on the data shown in Table 3 it can be determined that both the PAC and NDM fractions inhibit viral-induced haemagglutination. CHEP had no effect on virus induced hemagglutination.

TABLE 3

Effect of cranberry fractions on influenza virus induced hemagglutination

| Concentration[a] | CHEP | PAC | NDM |
|---|---|---|---|
| 500 | ±[b] | + | + |
| 250 | − | + | + |
| 125 | − | + | + |
| 62.5 | − | + | + |
| 31.2 | − | ± | + |
| 15.6 | − | ± | ± |
| 7.8 | − | ± | ± |
| 3.9 | − | − | ± |
| 1.95 | − | − | ± |
| Control | + | + | + |

[a] concentration [μg/ml] in the reaction mixture of the tested fractions.
[b] + = 100% inhibition of hemagglutination;
± = partial inhibition;
− = no inhibition In vivo Anti-Viral Activity Effect of Intranasal Administration (Inhalation) of Cranberry Constituents on Influenza-Virus Infection in Mice.

The virus (A/PR/8/34) was prepared at final concentration of $2\times10^6$ EID$_{50}$. NDM was prepared by dissolving the NDM in ddH$_2$O to a final concentration of 500 μg/ml. The total amount of inhaled solution was adjusted to 80 μl with PBS in the desired concentration. All inhalations were done under ketamine anesthesia with sterile tips.

Figure 3:
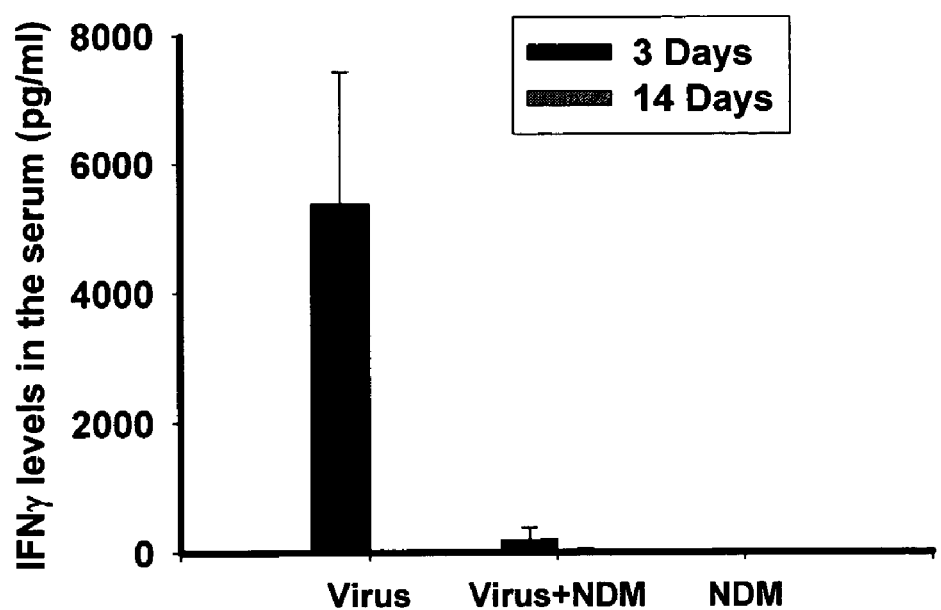

Three groups of male Balb/c mice 4-5 weeks old—10 mice each:
 Viral challenge: $10^6$ EID$_{50}$ in 80 μl of PBS
 Mixed NDM+Virus: 20 μg NDM mixed with virus in 80 μl of PBS before administration.
 Control: NDM 20 μg per animal in 80 μl of PBS
 Analyzed clinical parameters during 14 days of the experiment were:
 Blood for cytokines and anti-influenza antibodies
 Lungs for histology and virus titers The effect of intranasal administration (by inhalation) of cranberry constituents on influenza-virus infection in mice is summarized in the following Tables 4 to 7 and in FIG. 3. Specifically, the marked effect of intranasal administration of NDM on the infectious process induced by Influenza virus as demonstrated by:
 1. Morbidity and mortality (Table 4)
 2. Histopathology of the lungs (Table 5)
 3. Eradication of virus from the lungs (Table 6)
 4. The magnitude of anti-influenza antibodies in the serum (Table 7) and of cytokine response (FIG. 3).

TABLE 4

Effect of intranasal administration of cranberry derived NDM

| Experimental group | Number of symptomatic mice at days post infection | | | | | |
|---|---|---|---|---|---|---|
| | 0 H/S/D | 3 H/S/D | 7 H/S/D | 8 H/S/D | 9 H/S/D | 14 H/S/D |
| Virus | 9/0/0 | 0/9/0 | 0/9/0 | 0/9/0 | 0/7/2 | 0/0/9 |
| Virus + NDM | 9/0/0 | 9/0/0 | 9/0/0 | 9/0/0 | 9/0/0 | 9/0/0 |
| NDM | 9/0/0 | 9/0/0 | 9/0/0 | 9/0/0 | 9/0/0 | 9/0/0 |

H/S/D = Healthy/Sick/Dead

The effect of intranasal administration (inhalation) of cranberry constituents on lungs histopathology in influenza-virus infected mice is summarized in Table 5:

TABLE 5

Lungs histopathology

|  | Bronchial Lumen | Epithelial sloughing | Epithelial necrosis | Alveolar necrosis | Alveolar infiltration |
|---|---|---|---|---|---|
| Virus | Debris Neutrophils | Moderate | Moderate to marked | Moderate | Mild neutrophils |
| Virus + NDM | Clear | Rare | No | No | Minimal to no |

The effect of intranasal administration (inhalation) of cranberry constituents on virus recovery from lungs of influenza-virus infection in mice is summarized in Table 6

TABLE 6

Virus recovery

| | Hemagglutinating units of virus [a] | | |
|---|---|---|---|
| | Day 3 | Day 9 | Day 14 |
| Virus | 6.75 | 2.25 | Died |
| Virus + NDM | 2 | 0.5 | 0.5 |

[a] Numbers are the titers ($Log_{10}$) of the Influenza virus extracted from homogenized lungs after the indicated post infection days and determined by hemagglutination.

The effect of intranasal administration (inhalation) of cranberry constituents on virus antibodies in serum of influenza infection mice is shown in Table 7.

TABLE 7

Virus antibodies in serum

| | ELISA antiviral units | | |
|---|---|---|---|
| | Day 3 | Day 9 | Day 14 |
| Virus | <10 | 226.3 | Died |
| Virus + NDM | <10 | <10 | 6.1 |

FIG. 3 shows that the magnitude of cytokine response as a result of treatment with NMD markedly affected the infectious process induced by Influenza virus.

Additional animal experiments showed that the above effects of cranberry constituents were also observed when NDM was administered intranasaly after establishing viral infection (data not shown). Unexpectedly, cranberry constituents were as potent as those of Amantadine, Amantadine being a commercially available antiviral medicine (data not shown).

Taken together the above results show that cranberry constituents (NDM as well as PAC) applied directly to the port of the pathogen entry into the organ (mucosal surfaces), possess both protective and therapeutic effects.

The invention claimed is:

1. A method of treating a viral infection in a subject, comprising:
administering to a virally infected subject a therapeutically effective amount of a pharmaceutical composition comprising a polymeric material isolated from *Vaccinium macrocarpon* berry juice having a molecular weight of ≧12,000 kDa, wherein the viral infection is caused by an Influenza virus, and wherein the polymeric material, when assayed within a preparation containing the polymeric material at a concentration of 0.1 mg/ml therein, comprises less than 0.02 mg/ml of phenolic residues.

2. The method of claim 1, wherein the polymeric material isolated from *Vaccinium macrocarpon* berry juice comprises from 43% to 51% by weight carbon and from 4% to 5% by weight hydrogen.

3. The method of claim 1, wherein the polymeric material isolated from *Vaccinium macrocarpon* berry juice comprises:
from 43% to 51% by weight carbon;
from 4% to 5% by weight hydrogen; and
no nitrogen, no sulfur and no chlorine.

4. The method of claim 1, wherein the polymeric material isolated from *Vaccinium macrocarpon* berry juice exhibits an ultraviolet spectrum with a peak at 280 nm in neutral or acidic pH solutions, and wherein the peak is absent in alkali solutions.

5. The method of claim 1, wherein the polymeric material isolated from *Vaccinium macrocarpon* berry juice comprises at least one characteristic selected from the group consisting of
the polymeric material isolated from *Vaccinium macrocarpon* berry juice is capable of inhibiting viral adsorption to a susceptible host cell;
the polymeric material isolated from *Vaccinium macrocarpon* berry juice is capable of inhibiting viral invasion of a susceptible host cell; and
the polymeric material isolated from *Vaccinium macrocarpon* berry juice is capable of inhibiting viral replication in a host cell.

6. The method of claim 5, wherein the polymeric material isolated from *Vaccinium macrocarpon* berry juice comprises at least one characteristic selected from the group consisting of
the polymeric material isolated from *Vaccinium macrocarpon* berry juice is a non-dialyzable material (NDM) at a molecular weight cut-off of ≧12,000 kDa-14,000 kDa;
the polymeric material isolated from *Vaccinium macrocarpon* berry juice exhibits tannin-like properties;
the polymeric material isolated from *Vaccinium macrocarpon* berry juice is highly soluble in water;
the polymeric material isolated from *Vaccinium macrocarpon* berry juice is free from proteins, carbohydrates and fatty acids; and
the polymeric material isolated from *Vaccinium macrocarpon* berry juice contains 56.6% by weight carbon and 4.14% by weight hydrogen atoms.

7. The method of claim 5, wherein the viral adsorption to a susceptible host cell is through receptors comprising sialyl sugar chains present on the host cell's surface.

8. The method of claim 1, wherein the subject comprises a human or an animal.

9. The method of claim 1, wherein administering comprising intranasal administration.

10. The method of claim 1, wherein the polymeric material isolated from *Vaccinium macrocarpon* berry juice and having a molecular weight ≧12,000 kDa, is produced by the method comprising:

providing a *Vaccinium macrocarpon* berry juice concentrate;

subjecting the *Vaccinium macrocarpon* berry juice concentrate to dialysis at a molecular weight cut-off of $\geq$12,000 kDa-14,000 kDa; and collecting non-dialyzable material at the cut-off, to obtain the polymeric material isolated from *Vaccinium macrocarpon* berry juice and having a molecular weight $\geq$12,000 kDa.

* * * * *

UNITED STATES PATENT AND TRADEMARK OFFICE
CERTIFICATE OF CORRECTION

| | | |
|---|---|---|
| PATENT NO. | : 7,390,515 B2 | Page 1 of 1 |
| APPLICATION NO. | : 11/069041 | |
| DATED | : June 24, 2008 | |
| INVENTOR(S) | : Ervin I. Weiss et al. | |

It is certified that error appears in the above-identified patent and that said Letters Patent is hereby corrected as shown below:

On the Title Page

Please add in the following

Item (60) Provisional application No. 60/549,444, filed on March 3, 2004.

Signed and Sealed this
Third Day of January, 2012

David J. Kappos
*Director of the United States Patent and Trademark Office*